United States Patent [19]

Muthusamy

[11] Patent Number: 5,118,889
[45] Date of Patent: Jun. 2, 1992

[54] PROCESS FOR PREPARING ALLYL CHLORIDE

[75] Inventor: Duraisamy Muthusamy, Houston, Tex.

[73] Assignee: Shell Oil Company, Houston, Tex.

[21] Appl. No.: 779,667

[22] Filed: Oct. 21, 1991

[51] Int. Cl.$^5$ ............................................. K07L 17/02
[52] U.S. Cl. .................................................... 570/219
[58] Field of Search ......................................... 570/219

[56] References Cited

U.S. PATENT DOCUMENTS

| | | | |
|---|---|---|---|
| 2,130,084 | 9/1938 | Groll et al. | 260/654 |
| 2,207,193 | 7/1940 | Groll | 260/654 |
| 2,284,479 | 5/1942 | Rust et al. | 260/654 |
| 2,966,525 | 12/1960 | Steen | 260/654 |
| 3,454,661 | 7/1969 | Hornig et al. | 260/654 |
| 3,462,501 | 8/1969 | Hornig et al. | 260/654 |
| 3,489,816 | 1/1970 | Hornig et al. | 260/654 |
| 3,513,207 | 5/1970 | Hornig et al. | 260/654 |

OTHER PUBLICATIONS

K. A. Holbrook and J. S. Palmer, Gas-Phase Pyrolysis of 1,2-Dichoropropane, 23rd Mar., 1970.
G. J. Martens, M. Godfroid and L. ramoisy, Pyrolysis of 1,2-dichloropropane, International Journal of Chemical Kinetics, vol. II, 123-136 (1970).
Kirk-Othmer Encyclopedia of Chemical technology, 3rd Ed. vol. 5, Castor Oil to Chlorosulfuric Acid, pp. 763-773, 1979.

Primary Examiner—Marianne Cintins
Assistant Examiner—Jossie H. Nguyen

[57] ABSTRACT

The present disclosure is directed to upgrading to commercially useful products heavy ends by-products formed during the manufacture of allyl chloride. These heavy ends by-products are upgraded by first reacting the by-products with an alcohol in the presence of a base and subsequently pyrolyzing the resultant ethers to produce a mixture of allyl chloride and a carbonyl compound. This process improves the overall yield of the allyl chloride and forms commercially useful carbonyl compounds.

25 Claims, 1 Drawing Sheet

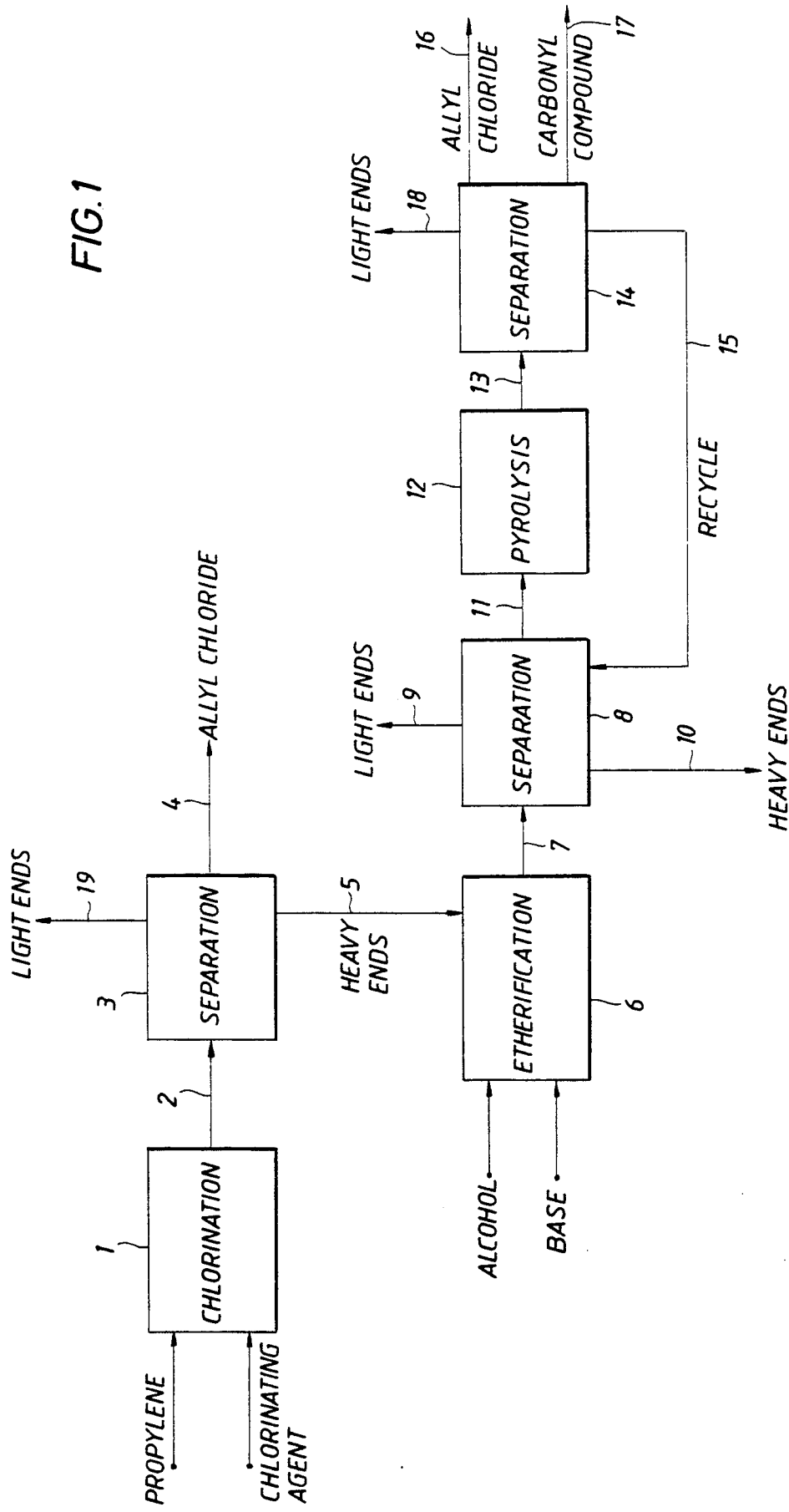

PROCESS FOR PREPARING ALLYL CHLORIDE

BACKGROUND OF THE INVENTION

This invention relates to the preparation of allyl chloride. In one aspect, the invention relates to upgrading by-products formed during the allyl chloride preparation to increase the yield of allyl chloride.

Allyl chloride is used commercially as the starting material in the manufacture of epichlorohydrin and glycerine. The principle commercial method for manufacturing allyl chloride is the thermal chlorination of propylene. During this process, propylene and chlorine are mixed at an elevated temperature rapidly enough to obtain reasonable yields of allyl chloride. However, this process forms by-products such as 1,2-dichloropropane, 1,3-dichloropropene, and other mono-, di-, and tri-chlorinated $C_3$'s. These by-products are used as the feed to preparation of more highly chlorinated hydrocarbons or are burned with heat and the chlorine values recovered as HCl. It would be desirable if these by-products could be converted to allyl chloride to obtain better yields of the desired product.

It is therefore an object of the present invention to provide an improved process for production of allyl chloride. It is a further object of the invention to upgrade by-products of an allyl chloride manufacturing process to useful products.

SUMMARY OF THE INVENTION

According to the invention, a process for the production of allyl chloride is provided, the process comprising the steps of:

(a) contacting a chlorinating agent and a stoichiometric excess of propylene at an elevated temperature at which allylic chlorine substitution predominantly takes place to produce a $C_3$-mixture-containing reaction effluent comprising allyl chloride, a dichloropropene and dichloropropane;

(b) removing at least a major portion of the allyl chloride from the reaction effluent;

(c) adding an alcohol and a base to the remaining reaction effluent and contacting the alcohol and the dichloropropene under conditions effective to form an ether intermediate;

(d) heating the ether intermediate containing reaction effluent at an effective temperature to react the ether intermediate and the dichlorpropane to produce allyl chloride; and (e) recovering the allyl chloride.

BRIEF DESCRIPTION OF THE DRAWINGS

FIG. 1 is a schematic flow diagram illustrating the invention process.

DETAILED DESCRIPTION OF THE INVENTION

In the invention process, allyl chloride is produced from heavy ends by-products formed during the manufacture of allyl chloride. Allyl chloride can be manufactured by high-temperature substitutive chlorination of propylene or by catalytic oxychlorination of propylene. Commercially, allyl chloride is produced by the high-temperature substitutive chlorination process. Heavy ends by-products from any of these allyl chloride manufacturing processes can be used as a starting material for the invention process.

In the general process, as shown in the schematic flow diagram of FIG. 1, a stoichiometric excess of propylene is mixed with a chlorinating agent in a chlorination zone 1 wherein the thermal chlorination or catalytic oxychlorination reaction occurs above room temperature in a reactor. The chlorinating agent can be chlorine, HCl or a mixture thereof depending on the process. The reactor effluent is passed via line 2 to a separation zone 3. Typically, in the separation zone, the reaction effluent is cooled prior to passage to a distillation column or an extraction vessel. A combination of distillation columns and/or extraction processes can be used to effectively separate the allyl chloride product, light ends and heavy ends. The heavy ends are passed via line 5 to etherification zone 6. In etherification zone 6, the heavy ends are mixed with an alcohol and a base and the etherification reaction is carried out in a reactor at a temperature within the range of about room temperature to about 250° C. and a pressure within the range of about atmospheric pressure to about 250 psig. The etherification reactor effluent is passed via line 7 to separation zone 8. Generally, in the separation zone, the etherification reaction effluent is cooled prior to passage of the effluent to a distillation column or an extraction vessel. A combination of distillation columns and/or extraction processes can be employed to separate the light ends and the heavy ends from the desired ether-containing stream. The ether-containing stream is passed to pyrolysis zone 12 via line 11. The ether-containing stream is heated in a pyrolysis furnace at an effective temperature for the ether to rearrange to allyl chloride and a carbonyl compound, which is generally a temperature within the range of about 400° to about 600° C., preferably about 450° to about 525° C. The pyrolysis effluent is passed via line 13 to separation zone 14. Generally, in the separation zone, the pyrolysis effluent is cooled by a quench column prior to passage of the effluent to a scrubber to remove the acid generated during the pyrolysis reaction. A combination of quenching column, condenser and/or distillation columns can be used to separate light ends, allyl chloride and carbonyl compounds. Allyl chloride can be recovered from zone 3 and from zone 14, respectively, via line 4 and line 16.

In the high-temperature substitutive chlorination process, chlorine is used as a chlorinating agent. The high-temperature chlorination process is described in U.S. Pat. No. 2,130,084, the disclosure of which is hereby incorporated by reference. It is desirable that both chlorine and propylene reactor feeds are dry and reasonably pure to limit yield losses. In the process, the feed is typically preheated before the reactants are mixed. The reaction can be carried out in an adiabatic reactor at an elevated temperature at which allylic chlorine substitution predominantly takes place but below the temperature at which substantial degradation such as cracking, splitting out of a hydrogen chloride, polymerization, etc., of the organic reactant and/or products is favored. Generally, the reactants are contacted at a temperature within the range of about 350° to about 675° C. Preferably, the reaction is carried out at a temperature within the range of about 480° C. to about 530° C., most preferably about 500° to about 510° C. and at a pressure of about 20 psig. The feed can be introduced under conventional instrument control through a suitable mixing nozzle. Reaction temperature can be controlled by balancing the feed mole ratio and the propylene preheat temperature. For example, a reaction temperature of about 500° C. can be maintained by preheating propylene to about 110° C. at a propylene to chlorine mole ratio of 2:1, while preheating to about 340° C. may be necessary at a ratio of 4:1. Optionally, the reaction can be carried out in the presence of a free radical or a free radical promoter as described in U.S. Pat. No. 2,284,479. The reactor effluent includes allyl chloride, 1,2-dichloropropane and dichloropropenes. The reactor effluent is generally cooled in stages using heat exchangers. The effluent is typically cooled to a temperature within the range of about 10° C. to about 50° C. in heat exchangers.

Allyl chloride is separated from the product stream, typically by a series of fractionations. In a typical fractionation, hydrogen chloride and propylene are removed in a fractionating column, then the organic chloride fraction is separated in a two-step distillation. Other separation methods such as preferential absorption or extraction can be used. In the fractionating column, the overhead stream is split; propylene is recycled and hydrogen chloride is taken off to other uses. Fractional distillation may be employed if anhydrous acid is desired, or hydrogen chloride can be selectively absorbed into water to produce hydrochloric acid. Generally, in the distillation of the organic chloride fraction, low-boiling constituents are taken overhead in the first column and allyl chloride in the second. The heavy-boiling fraction is generally taken off as a bottoms product (heavy ends by-product) in the second column, which is made up largely of dichloropropenes and dichloropropane as listed in Table 1.

In a catalytic oxychlorination process, allyl chloride is prepared by the reaction of oxygen and hydrogen chloride with propylene in the presence of an oxychlorination catalyst at a temperature effective to produce allyl chloride. Suitable catalysts are described in U.S. Pat. No. 2,966,525; U.S. Pat. No. 3,454,661; U.S. Pat. No. 3,462,501; U.S. Pat. No. 3,513,207, U.S. Pat. No. 3,489,816 for example. Suitable catalysts include, for example, lithium chloride supported on pumice, elementary tellurium, platinum, ruthenium, rhodium, palladium, iridium, palladium oxide, manganese oxide, chloride of copper, samarium, chromium, manganese or praseodynium, manganese ore or tellurium-, palladium-, or platinium-containing catalyst (optionally combined with one or more of alkali metal salt, Fe—, Cu—, Ni—, Pb—, Ag—, Pd— and Pt— compounds) optionally supported on an inert carrier such as aluminum oxide, bentonite, aluminum silicate, sandstone, carbon, silica gel, pumice, asbestos, feldspar, zeolite or silicon carbide. In a general process, the substitutive chlorination can be effected by mixing the propylene with hydrogen chloride and air or oxygen and passing the mixture in contact with the catalyst in a heated reaction chamber. If desired, the mixture may be introduced into the reaction zone in three separate streams or the air or oxygen may be introduced into a mixture of propylene and hydrogen chloride. Reaction temperature varies depending on the catalyst used. For example, the reaction temperature should be above 400° C. when lithium chloride is used; the reaction temperature is preferably within a range of about 50° to about 350° C. when tellurium or Group VIII metals are used.

The reactor effluent from the catalytic oxychlorination reaction can include allyl chloride, dichloropropane, dichloropropene and other chlorocarbon by-products similar to the reactor effluent from the high-temperature chlorination process. Depending on the catalyst used and the temperature used, the ratio of the products and the various by-products formed will vary. The products and the by-products can be separated as described above.

It has been found that the heavy ends by-products formed from the chlorination reaction can be upgraded to allyl chloride and carbonyl compounds by an etherification/pyrolysis process. In the invention process, the by-product stream is contacted with an alcohol in the presence of a base in a reactor. Suitable bases are alkali metal hydroxides, alkaline earth metal hydroxides, alkali metal alkoxides, alkaline earth metal alkoxides, alkali metal carbonates, and alkaline earth metal carbonates. Examples of such bases include lime, NaOH, KOH, LiOH, $Mg(OH)_2$, $Na_2CO_3$, $K_2CO_3$, $Li_2CO_3$, $MgCO_3$, NaOR, KOR, $Mg(OR)_2$, $Ca(OR)_2$ and LiOR wherein R is an alkyl group corresponding to the alcohol reactant used. Lime is preferred for use in the invention process because of its low cost and availability. Primary alcohols are preferred over secondary alcohols for the invention process for ease of reaction. Preferred alcohols are $C_1$-$C_5$ alcohols. Examples of suitable alcohols include methanol, ethanol, propanol, n-butanol, n-pentanol and sec-butanol. Methanol is preferred for the invention process because of its low cost and availability.

The base should be present in an amount effective to react dichloropropene with alcohol to produce the corresponding ether. Generally, the base is present in an equivalents ratio of base to dichloropropene of about 1.0 to about 3.0, preferably about 1.0 to about 1.3. Generally, the alcohol is present in excess of stoichiometry. Preferably the alcohol is present in an equivalents ratio of alcohol to dichloropropene of about 1 to about 14, most preferably about 1 to about 3. It is optional to pre-mix the alcohol and the base prior to addition to the by-product stream.

Generally, the reaction is carried out at a temperature within the range of room temperature to about 250° C. and a pressure within the range of atmospheric pressure to 500 psig. A temperature within the range of about 60° C. to about 150° C. and a pressure within the range of atmospheric pressure to about 250 psig are preferred. The temperature and pressure will vary depending on the alcohol used. For example, for methanol a temperature within the range of about 140° C. to about 155° C. and a pressure within the range of about 200 psig to about 240 psig are preferred. The temperature is preferably controlled at a temperature below about 150° C. to keep the dichloropropane in the heavy ends by-product stream from reacting in the etherification zone. The reaction can be carried out in a batch process or in a continuous process. In the etherification zone, dichloropropenes and alcohol are allowed to react to form the corresponding ether intermediates as shown in Table 1. The effluent of the etherification reactor includes the resultant ether intermediates and unreacted dichloropropane.

In the separation zone, salts formed from the etherification reaction are generally extracted from the effluent. For example, when lime is used as the base, the extraction can be carried out by adding water to the effluent, and separating the water layer containing $CaCl_2$ and unreacted alcohol and the organic layer containing the ether intermediates and dichloropropane. Water extraction can also be used for extraction of other salts formed during the etherification reaction from other bases. Optionally, further extraction steps and/or distillation steps can be employed in the separation zone to further purify the ether intermediates from light ends (e.g., unreacted alcohol and monochloropropenes) and heavy ends (e.g., tar). The purified ether-containing effluent can generally be dried before further processing. The purified ether-containing effluent can be stored or accumulated prior to the pyrolysis step.

In the pyrolysis zone, the purified ether-containing effluent is heated to an effective temperature to form allyl chloride in a pyrolysis furnace. The ether intermediates rearrange to form allyl chloride and carbonyl compounds as shown in Table 1. The carbonyl compound formed will depend on the corresponding alcohol used. For example, when secbutanol is used, methyl ethyl ketone is formed; when methanol is used, formaldehyde is formed. Dichloropropane rearranges to allyl chloride, allyl chloride isomers and HCl. The pyrolysis is generally carried out at a temperature within the range of about 400° C. to about 600° C., preferably about 450° C. to about 525° C.

In the separation zone, the pyrolyzed reaction product stream can be passed through at least one or more of a quench column, condenser, extraction vessel and distillation column to separate the resultant allyl chloride, carbonyl compound and light ends from the pyrolyzed reaction product stream which contains unrearranged ether, unreacted dichloropropane, tar, and the like which can be recycled to the etherification zone or separation zone. Typically, a scrubber is also used to extract or neutralize the acid generated during the process. Alternatively, a fractionation column can be used to distill the acid off. In one embodiment, subsequent to quenching and condensing, allyl chloride and light ends can be separated by distillation. A two-step distillation process as described above can also be used to separate allyl chloride. The carbonyl compounds can be separated by distillation or in a scrubber.

The separated allyl chloride can be recovered, increasing the overall yield of allyl chloride in the manufacturing process. The allyl chloride removed from chlorination zone 1 and pyrolysis zone 12 can be separately recovered or combined in a crude form (e.g., prior to the second distillation step) and recovered.

The following examples demonstrate the etherification/pyrolysis process in an allyl chloride synthesis by-product upgrading scheme according to the invention process. Examples 1-5 demonstrate the etherification step and Examples 6-9 demonstrate the pyrolysis step of the invention process.

The etherification product samples were diluted with water to dissolve the inorganic salts and were then phase separated, and the organic phase was analyzed by CG. The pyrolysis product samples containing HCl were prepared for CG analyses by shaking with water to remove the HCl, and drying the organic phase by passing it through a small bed of sodium sulfate held in a 2-ml disposable pipette. Area % were normalized after exclusion of the unreacted excess alcohol.

EXAMPLE 1

This example demonstrates etherification of dichloropropene (DCP) with sec-butanol in the presence of various bases.

Run 1

In a 500 ml round-bottom flask equipped with a reflux condenser, thermometer, heating mantle, and magnetic stirrer, 50.5 g of 1,3-dichloropropene (1,3-DCP), 150 g of sec-butyl alcohol, 50.0 g of $Ca(OH)_2$ and 50 g of water were placed. The mixture was stirred and heated to a reflux for 2.5 hours. The reaction temperature remained at 85°-87° C. throughout the reaction. A sample of the organic phase was analyzed by gas chromatography (GC) to determine the composition. The results are shown in Table 2.

Run 2

In a 2000 ml flask equipped as in Example 1, 400.9 g of 50% w NaOH solution in water, 298.3 g of sec-butyl alcohol, 333.8 g of 1,3-DCP and 0.30 g of tetrabutylammonium hydroxide phase transfer catalyst were charged. The mixture was stirred and heated to reflux. The reaction temperature remained at 97°-95° C. throughout the reaction. The mixture was cooled to room temperature after 3 hours and analyzed by GC. The results are shown in Table 2.

Run 3

In a 500 ml flask equipped as in Example 1, 54.3 g of 46.7% w NaOH solution in water, 49.8 g of sec-butyl alcohol, 54.1 g of 1,3-DCP and 0.52 g of tetrabutylammonium hydroxide phase transfer catalyst were charged. The mixture was stirred and heated to reflux. The mixture was cooled to room temperature after 2 hours and analyzed by GC. The reaction temperature remained at 85°-81° C. throughout the reaction. The results are shown in Table 2.

Run 4

TABLE 1

| Composition and Etherification and Pyrolysis of Heavy Ends[a,b,c] | | | |
|---|---|---|---|
| Heavy Ends Component | (% w) | Ether Products | Pyrolysis Products |
| $ClCH=CH-CH_2Cl$ | (57.6) | $ClCH=CH-CH_2-OR$ | $CH_2=CH-CH_2Cl$ + Carbonyl Compound |
| $CH_2=CH-CHCl_2$ | (4.0) | $ClCH=CH-CH_2-OR$ | $CH_2=CH-CH_2Cl$ + Carbonyl Compound |
| $CH_2=CH(Cl)-CH_2-Cl$ | (5.1) | $CH_2=CH(Cl)-CH_2OR$ | $CH_2=CH(Cl)-CH_3$ + Carbonyl Compound |
| $CH_3-CH(Cl)-CH_2Cl$ | (27.7) | $CH_3-CH(Cl)-CH_2Cl$ | $CH_2=CH-CH_2Cl$ + $CH_3-CH=CHCl$ + HCl |

[a]The composition may vary slightly depending on the operating conditions of the chlorination reactor.
[b]Other components, not listed above but whose structures are known, are benzene (0.2% w), two isomers of 1,3,3-trichloropropene (1% w) each, and 1,2,3-trichloropropane (1% w).
[c]R = straight or branched chain alkyl group from the corresponding alcohols used in the etherification step.

In a 200 ml flask equipped as in Example 1, 3.0 g (0.13 mole) of sodium metal pieces were slowly added to 79.8 g of sec-butyl alcohol under nitrogen atmosphere and allowed to dissolve. 14.2 g (0.125 mole) of 1,3-DCP were added at 30° C. Samples were drawn after 1 and 4 hours and analyzed by GC. The results are shown in Table 2.

Run 5

A large batch of the reaction between 1,3-DCP and sodium sec-butoxide was carried out using 35.0 g of sodium metal. The reaction was allowed to proceed at 30° C. for 19 hours and then the mixture was refluxed for 3 hours to complete the reaction. The reaction product was cooled, hydrolyzed by adding water, and phase separated. Another batch was similarly carried out. The products were combined and washed several times with water to remove as much sec-butyl alcohol (SBA) as possible. The organic phase was distilled with the use of a 7-tray Oldershaw column under reduced pressure (25 mm Hg). Fractions boiling at 55°–56° C. were collected and combined to get 165 g of a product which was 98.0% pure. The SBA content was 0.13%. The purified product was characterized by proton and carbon-13 NMR analyses. The % conversion and % area selectivity are shown in Table 2.

alcohol is faster and more selective to the desired ether intermediate compared to sec-butyl alcohol.

EXAMPLE 3

This example demonstrates etherification of DCP with ethanol in the presence of NaOH as base.

In a 100 ml round-bottom flask equipped with a reflux condenser, thermometer, rubber septum, and magnetic stirrer, 6.4 g of 97% NaOH pellets were added and allowed to dissolve in absolute ethanol and water in a mole ratio according to Table 3 under nitrogen atmosphere. 1,3-DCP was added to the mixture maintained at 65°–68° C. with a water bath in an amount according

TABLE 2

Synthesis of 3-Chloroallyl sec-Butyl Ether (3-CASBE)

| Run # | Base | Rxn Time (Hours) | Temp (°C.) | % Conv 1,3-DCP | % Area Selectivity | | | | | |
|---|---|---|---|---|---|---|---|---|---|---|
| | | | | | 3-CASBE | $C_3H_3Cl$ | $C_7H_{12}O$ | 3-CAA[a] | 3-CAE[b] | Others |
| 1 | Ca(OH)$_2$ | 2.5 | 85 | 12 | 18 | 0 | 1 | 29 | 0 | 53 |
| 2 | 50% NaOH | 3 | 97 | 38 | 23 | 25 | 0 | 2 | 14 | 36 |
| 3 | 47% NaOH | 2 | 80 | 86 | 39 | 17 | 2 | 6 | 25 | 11 |
| 4 | C$_4$H$_9$ONa | 1 | 30 | 31 | 58 | 1 | 0 | 0 | 1 | 39 |
|   | C$_4$H$_9$ONa | 4 | 30 | 81 | 83 | 2 | 1 | 0 | 3 | 11 |
| 5 | C$_4$H$_9$ONa | 19 | 30 | 88 | 83 | 3 | 2 | 0 | 2 | 11 |
|   | C$_4$H$_9$ONa | +3 Hrs | Reflux | 99 | 67 | 3 | 17 | 0 | 1 | 11 |

[a]3-chloroallyl alcohol
[b]3-chloroallyl ether

As shown in Table 2, the product distribution and the % conversion of 1,3-DCP is sensitive to the base used, reaction temperature and reaction time. Up to 99% conversion of the reactant 1,3-DCP can be obtained when sodium sec-butoxide is used as a base and heated for 22 hours as shown in run 5.

to Table 3. The reaction temperature rose sharply to 78° C. during the first few minutes and then fell back to the bath temperature. Samples were removed after 17, 40, 90 and 180 minutes of reaction time and analyzed by GC. The mole ratios of the reagents, % 1,3-DCP conversion and ether selectivity are shown in Table 3.

TABLE 3

Etherification of 1,3-DCP with EtOH and NaOH

| Run # | Rxn Time (min) | Rxn Temp[a] (°C.) | Mole Ratios | | | | % Conv[b] 1,3-DCP | % Select[b] 3-CAEE[c] |
|---|---|---|---|---|---|---|---|---|
| | | | 1,3-DCP | EtOH | H$_2$O | NaOH | | |
| 1 | 0 | 68 | 1.00 | 5.81 | 1.85 | 1.00 | 0 | |
|   | 17 | " | | | | | 92 | 95 |
|   | 40 | " | | | | | 96 | 95 |
|   | 90 | " | | | | | 98 | 96 |
|   | 180 | " | | | | | 99 | 94 |
| 2 | 0 | 68 | 0.92 | 5.81 | 1.85 | 1.00 | 0 | |
|   | 17 | " | | | | | 89 | 98 |
|   | 40 | " | | | | | 94 | 96 |
|   | 90 | " | | | | | 99 | 96 |
|   | 180 | " | | | | | 100 | 94 |
| 3 | 0 | 65 | 0.98 | 5.67 | 3.98 | 1.00 | 0 | |
|   | 17 | 66 | | | | | 81 | 93 |
|   | 40 | " | | | | | 90 | 92 |
|   | 90 | " | | | | | 96 | 92 |
|   | 180 | " | | | | | 99 | 92 |
| 4 | 0 | 65 | 0.98 | 9.59 | 4.51 | 1.00 | 0 | |
|   | 17 | " | | | | | 86 | 94 |
|   | 40 | " | | | | | 94 | 94 |
|   | 90 | " | | | | | 97 | 94 |
|   | 180 | 64 | | | | | 99 | 93 |

[a]See Experimental.
[b]Based on area %.
[c]3-chloroallyl ethyl ether.

EXAMPLE 2

This example demonstrates etherification of DCP with n-butyl alcohol in the presence of sodium n-butoxide as base.

Reaction was carried out in a similar manner to run 4 of Example 1, except 90.3 g of n-butyl alcohol was used instead of sec-butyl alcohol, 3.04 g sodium metal (0.13 mole) instead of 3.0 g and 14.7 g (0.13 mole) of 1,3-DCP were added at 50° C. At the end of 2 hours, 89% of 1,3-DCP was converted. The reaction with n-butyl As shown in Table 3, selectivity is adversely affected by an increase in water content compared to the amount of ethanol when NaOH is used as the base.

EXAMPLE 4

This example demonstrates etherification of DCP with methanol in the presence of lime as base.

200 g of methanol, 50.0 g of 1,3-DCP and 15.2 g of lime were added to a 500 ml Hastelloy-B zipperclave equipped with a stirrer, temperature controller, pressure gauge, and a sampling line. The zipperclave was purged four times with 100 psig of nitrogen gas. The mixture was stirred and heated to 150° C. over a period of 20 minutes. The pressure was 220 psig at the reaction temperature of 150° C. After 40 minutes at 150° C. (total of 1 hour reaction time), the mixture was cooled to room temperature over a period of 5-8 minutes to obtain a sample for analysis. The mixture was reheated at 150° C. and periodically cooled to obtain a sample. Samples were obtained after 1, 2, 3 and 4 hours of reaction time and analyzed by GC. The % conversion and selectivity are shown in Table 4.

TABLE 4

Etherification of 1,3-DCP with Methanol and Lime

| Rxn Time (hour) | Rxn Temp[a] (°C.) | % Conv[b] 1,3-DCP | % Select[b] 3-CAME[c] |
|---|---|---|---|
| 1 | 150 | 77 | 99 |
| 2 | 150 | 96 | 99 |
| 3 | 150 | 98 | 96 |
| 4 | 150 | 100 | 95 |

[a]See Experimental.
[b]Based on area %.
[c]3-Chloroallyl methyl ether.

As shown in Table 4, 1,3-DCP can be effectively converted to the corresponding ether with methanol. It is also shown that lime is an effective base converting 1,3-DCP to 3-chloroallyl methyl ether in the range of 95-99% with a conversion of up to 100%.

EXAMPLE 5

This example demonstrates etherification of a heavy end by-product stream obtained from a high-temperature substitutive chlorination process.

Reaction was carried out in a similar manner to Example 4 except 200.4 g of methanol, 72.8 g of flashed heavy ends and 15.2 g of lime were allowed to react. The composition of the flashed heavy ends and composition and % conversion of reaction product mixture at varying run times are shown in Table 5.

Thus, there is no need to separate 1,2-DCPA in the invention process.

EXAMPLE 6

This example demonstrates the pyrolysis step of the ether-intermediate, 3-chloroallyl sec-butyl ether (3-CASBE) formed by the etherification of 1,3-DCP with sec-butyl alcohol in the presence of sodium sec-butoxide.

A sample of 3-CASBE was prepared as follows. The reaction product from run 5 of Example 1 (prior to hydrolysis) was cooled, and hydrolyzed by adding water and phase separated. Another batch of 3-CASBE was similarly prepared. Both batches were combined and washed with water to remove as much sec-butyl alcohol as possible. The organic phase was distilled with the use of a 7-tray Oldershaw column under reduced pressure (25 mmHg). Fractions boiling at 55°-56° C. were collected to obtain 165 g of product which was 98.0% pure 3-chloroallyl sec-butyl ether. Sec-butyl alcohol content was 0.13%.

3-CASBE collected above was pyrolyzed at a temperature, liquid hourly space velocity (LHSV) in grams of feed per ml of reactor volume per hour and run time according to Table 6. Samples were collected and analyzed by GC. HCl was generated during the pyrolysis. The % conversion and selectivity are shown in Table 6.

TABLE 6

Pyrolysis of 3-CASBE to AC and MEK

| Run # | Run Time (min) | LHSV (g/ml/Hr) | Temp (°C.) | % Conv 3-CASBE | % Area Selectivity AC + MEK | C4[a] | Others |
|---|---|---|---|---|---|---|---|
| 1 | 6.6 | 7.5 | 500 | 12 | 89 | 6 | 5 |
|  | 11.0 | " | " | 12 | 91 | 6 | 4 |
|  | 15.0 | " | " | 11 | 90 | 6 | 4 |
| 2 | 5.0 | 3.2 | 510 | 17 | 91 | 3 | 6 |
|  | 10.0 | " | " | 17 | 92 | 3 | 4 |
|  | 15.0 | " | " | 17 | 93 | 4 | 4 |
|  | 20.0 | " | " | 16 | 93 | 4 | 3 |
| 3 | 10.0 | 2.1 | 510 | 16 | 86 | 3 | 11 |
|  | 20.0 | " | " | 17 | 88 | 4 | 8 |
|  | 30.0 | " | " | 16 | 91 | 5 | 4 |
| 4 | 11.0 | 2.4 | 520 | 21 | 92 | 3 | 6 |
|  | 20.0 | " | " | 21 | 92 | 3 | 5 |
|  | 30.0 | " | " | 24 | 92 | 3 | 5 |
| 5 | 10.0 | 2.0 | 550 | 46 | 86 | 1 | 13 |
|  | 20.0 | " | " | 49 | 88 | 2 | 10 |

TABLE 5

Etherification of Heavy Ends By-Products with Methanol and Lime

| Run Time (hour) | Run Temp (°C.) | % Area Composition |  |  |  |  |  |  |  |  |  |
|---|---|---|---|---|---|---|---|---|---|---|---|
|  |  | CP[a] | AC | Benz | 2-CAME | 3,3-DCP | 1,2-DCPA | 2,3-DCP | c3-CAME | t3-CAME | c1,3-DCP | t1,3-DCP |
| 0 |  | 0.0 | 0.5 | 0.8 | 0.0 | 3.1 | 31.4 | 4.9 | 0.0 | 0.0 | 29.2 | 25.5 |
| 1 | 150 | 0.7 | 0.3 | 0.8 | 0.5 | 1.6 | 30.1 | 4.4 | 19.6 | 21.1 | 10.4 | 6.1 |
| 2 | 150 | 1.0 | 0.3 | 0.8 | 1.0 | 0.5 | 29.3 | 3.9 | 26.8 | 26.1 | 3.8 | 1.6 |
| 3 | 150 | 1.0 | 0.1 | 0.9 | 1.6 | 0.4 | 30.1 | 3.3 | 29.5 | 26.4 | 1.1 | 0.3 |
| 4 | 150 | 1.1 | 0.0 | 1.0 | 2.4 | 0.4 | 31.0 | 2.5 | 30.4 | 26.4 | 0.2 | 0.3 |

| Run Time (hour) | Run Temp (°C.) | % Area Composition |  |  |  |  |  | % Conversion |  |  |  |
|---|---|---|---|---|---|---|---|---|---|---|---|
|  |  | Unknown | TCP | TCPA | 3-CAA | 3-CAE | Others | 3,3-DCP | 2,3-DCP | c1,3-DCP | t1,3-DCP |
| 0 |  | 0.0 | 1.0 | 0.7 | 0.2 | 0.0 | 2.5 |  |  |  |  |
| 1 | 150 | 0.9 | 0.5 | 0.0 | 0.1 | 0.5 | 2.3 | 47.9 | 10.2 | 64.3 | 76.1 |
| 2 | 150 | 1.0 | 0.2 | 0.0 | 0.1 | 0.6 | 3.0 | 82.6 | 20.1 | 87.1 | 93.7 |
| 3 | 150 | 1.1 | 0.3 | 0.0 | 0.1 | 0.2 | 3.6 | 87.1 | 32.5 | 96.3 | 98.9 |
| 4 | 150 | 0.1 | 0.0 | 0.0 | 0.1 | 0.2 | 3.9 | 85.7 | 48.9 | 99.5 | 99.0 |

[a]Includes 1- and 2-chloropropenes.
TCP = 1,3,3-trichloropropenes; TCPA = 1,2,3-trichloropropane.

As shown in Table 5, 1,3-DCP and 3,3-DCP can be converted effectively to the corresponding ether in a heavy ends mixture. 1,3-DCP was converted up to 99.5 and 99.0% for cis and trans-1,3 DCP, respectively, and 3,3-DCP was converted up to 87.1%. These results show that the etherification step can be accomplished by using unfractionated crude heavy ends feed, excess alcohol, and lime as base. It also shows that 1,2-dichloropropane (1,2-DCPA) in the heavy ends is mostly preserved under the etherification conditions.

TABLE 6-continued

| | | Pyrolysis of 3-CASBE to AC and MEK | | | | | |
|---|---|---|---|---|---|---|---|
| Run # | Run Time (min) | LHSV (g/ml/Hr) | Temp (°C.) | % Conv 3-CASBE | AC + MEK | % Area Selectivity C4[a] | Others |
| | 30.0 | " | " | 50 | 88 | 2 | 10 |

[a]C4 = butylene.

As shown in Table 6, as the pyrolysis temperature increases from 500° C. to 550° C., the % conversion of 3-CASBE increases. However, at 550° C., the selectivity to allyl chloride and methyl ethyl ketone may slightly decrease. At 510° C. and LHSV of 3.2 g/ml/hr, the pyrolysis of 3-CASBE gave allyl chloride (AC) and methyl ethyl ketone combined selectivity of 91-93%. At 520° C. and LHSV of 2.4 g/ml/hr, conversion increased up to 24% with a selectivity of 92%.

EXAMPLE 7

This example demonstrates pyrolysis of the ether-intermediate, 3-chloroallyl n-butyl ether (3-CANBE), formed by the etherification of 1,3-DCP with n-butyl alcohol in the presence of sodium n-butoxide.

A batch of 3-CANBE was prepared in a similar manner to Example 2, except 1500 g of n-butyl alcohol, 50.5 g of sodium and 241.8 g of 1,3-DCP were used and the reaction was allowed to proceed to near complete conversion. The reaction mixture was hydrolyzed and phase separated by adding one liter of water. 275 g of benzene was added to the organic phase and distilled to separate water as an azeotrope with the use of a Dean-Stork apparatus. After all the water (200 ml) had been removed, the product was fractionated using a 15-tray Oldershaw column. The residue, 282 g, was distilled under reduced pressure (20 mmHg). Fractions boiling between 55°-63° C. were collected as feed. The feed contained 47.6% cis-3-CANBE, 51.3% trans-3-CANBE, and 0.5% n-butyl alcohol.

The feed collected above was pyrolyzed at a temperature, LHSV (grams of feed per ml of reactor volume per hour) and run time according to Table 7. Samples were collected and analyzed by GC. HCl was generated during the pyrolysis. The % conversion and selectivity are shown in Table 7.

TABLE 7

| | | Pyrolysis of 3-CANBE to AC and NBAD[a] | | | | |
|---|---|---|---|---|---|---|
| Run # | Run Time (min) | LHSV (g/ml/Hr) | Temp (°C.) | % Conv 3-CANBE | % mol Selectivity[b] AC | NBAD[a] |
| 1 | 35 | 2.0 | 500 | 16 | 71 | 63 |
| | 68 | " | " | 15 | 78 | 70 |
| | 98 | " | " | 15 | 81 | 74 |
| 2 | 73 | 0.8 | 473 | 20 | 63 | 76 |
| | 120 | " | " | 19 | 71 | 85 |
| 3 | 60 | 0.8 | 450 | 3 | 49 | 72 |
| | 120 | " | " | 7 | 69 | 77 |
| | 180 | " | " | 7 | 73 | 78 |

[a]NBAD = n-butyraldehyde
[b]Based on GC analysis which included response factors.

As shown in Table 7, the ratio of mol% selectivity of allyl chloride (AC) to n-butyl aldehyde is close to 1:1 but varies depending on the temperature and LHSV. The mol% selectivities and % conversion of allyl chloride and NBAD increases with increased temperature. The mol% selectivities of allyl chloride and NBAD increase with increased run time. The selectivity is expected to improve as the pyrolysis reaction is run longer, which passivates the reactor surface and minimizes side reactions.

EXAMPLE 8

This example demonstrates pyrolysis of the ether-intermediate 3-chloroallyl methyl ether (3-CAME) formed by the etherification of 1,3-DCP with methyl alcohol in the presence of sodium hydroxide.

In a 5-liter round-bottom flask equipped with a mechanical stirrer, reflux condenser, and thermometer, 325 g of NaOH pellets (97% assay) were slowly added and dissolved in 1500 g of methanol. 800 g of 1,3-DCP was added to this mixture over a period of one hour. The reaction mixture was maintained at reflux temperature (65°-66° C.) for one hour and at room temperature overnight. The reaction mixture was diluted with water to dissolve all the salt. 500 ml of pentane was added and the mixture phase separated. The organic phase was washed four times with 250 ml of water. The washings were combined and distilled. The distillate was mixed with 150 ml of pentane and washed four times with 50 ml of water. The pentane solutions were combined, dried over MgSO4, and distilled using a 15-tray Oldershaw column. Fractions boiling in the 107° to 111° C. temperature range were collected as feed. The feed contained 48.5% cis-3-CAME, 49.8% trans-3-CAME, and 1.7% impurities.

The feed collected above was pyrolyzed at a temperature, LHSV (ml of feed per ml of reactor volume per hour) and run time according to Table 8. Samples were collected and analyzed by GC. HCl was generated during the pyrolysis. The % conversion and selectivity are shown in Table 8.

TABLE 8

| | | Pyrolysis of 3-CAME | | | | | |
|---|---|---|---|---|---|---|---|
| Run # | Feed | Run Time (hour) | LHSV (ml/ml/hr) | Temp (°) | N2/Feed (mol/mol) | % Conv | % mol Select to AC[a] |
| 1 | 3-CAME | 3.0 | 0.8 | 500 | 0.0 | 16.8 | 58 |
| 2 | 3-CAME | 3.0 | 0.8 | 510 | 1.7 | 11.5 | 78 |

[a]Based on GC analysis which included response factors.

As shown in Table 8, the % conversion of 3-CAME is between 11 and 17%, however % selectivity to allyl chloride is increased to 78% with the use of N2 diluent. Further, as seen in Example 7, the % selectivity is expected to increase with increase in pyrolysis run time. It is expected that the yield of allyl chloride can be improved by varying LHSV, temperature and N2/feed ratio.

EXAMPLE 9

This example demonstrates co-pyrolysis of the ether-intermediate 3-CAME and 1,2-dichloropropane (1,2-DCPA).

A synthetic feed mixture containing 30.1 w % 1,2-DCPA and 69.9 w % 3-CAME was made using distilled 1,2-DCPA and 3-CAME. This feed was pyrolyzed at a temperature, LHSV and run time according to Table 9. Samples were collected and analyzed by GC. HCl was generated during the pyrolysis. The % conversion and selectivity are shown in Table 9.

TABLE 9

Pyrolysis of 3-CAME and 1,2-DCPA to AC and Formaldehyde

| Run # | Feed[a] | Run Time (hour) | LHSV (ml/ml/hr) | Temp (°C.) | % Conv 3-CAME | % Conv 1,2-DCPA | % Conv Overall | % mol Select to AC[b] 3-CAME | % mol Select to AC[b] 1,2-DCPA[c] |
|---|---|---|---|---|---|---|---|---|---|
| 1 | Ether/DCPA | 4.0 | 0.8 | 500 | 17.1 | 10.2 | 15.0 | 60 | 64 |
|   |            | 6.6 | "   | 510 | 23.5 | 18.2 | 21.9 | 56 | 64 |
| 2 | Ether/DCPA | 6.0 | 0.8 | 510 | 21.4 | 16.4 | 19.9 | 54 | 64 |

[a]The ether/DCPA feed mixture contained 68.65% 3-CAME and 30.1% 1,2-DCPA
[b]Based on GC analysis which included response factors.
[c]An AC selectivity of 64% mol was assumed.

As shown in Table 9, both 3-CAME and 1,2-DCPA can be converted in a mixed feed to allyl chloride by pyrolysis. With the adjustment of residence time, temperature, and addition of $N_2$ diluent, the overall yield of the starting material to allyl chloride is expected to increase.

It is expected that by etherification/pyrolysis processing of heavy ends containing 1,3-DCP and 1,2-DCPA, a similar result can be obtained, effectively converting 1,3-DCP and 1,2-DCPA to allyl chloride and a carbonyl compound without separating 1,2-DCPA during the etherification step.

I claim:

1. A process for the production of allyl chloride comprising the steps of:
   (a) contacting a stoichiometric excess of propylene and a chlorinating agent at an elevated temperature at which allylic chlorine substitution predominantly takes place to produce a $C_3$-mixture-containing reaction effluent comprising allyl chloride, a dichloropropene and dichloropropane;
   (b) removing at least a major portion of the allyl chloride from the reaction effluent;
   (c) adding an alcohol and at least about one equivalent of a base, based on dichloropropene, to the remaining reaction effluent and contacting the alcohol and the dichloropropene under conditions effective to form an ether intermediate;
   (d) heating the ether intermediate containing reaction effluent at an effective temperature to react the ether intermediate and the dichloropropane to produce allyl chloride; and
   (e) recovering the allyl chloride.

2. The process of claim 1 in which the chlorinating agent is selected from the group consisting of chlorine, HCl and mixtures thereof.

3. The process of claim 2 in which propylene and chlorine are contacted at a temperature within the range of 350° to 675° C.

4. The process of claim 2 in which propylene and HCl are contacted in the presence of an oxychlorination catalyst.

5. The process of claim 1 in which the base is selected from the group consisting of alkali metal hydroxides, alkaline earth metal hydroxides, alkali metal alkoxides, alkaline earth metal alkoxides, alkali metal carbonates and alkaline earth metal carbonates.

6. The process of claim 5 in which the base is selected from the group consisting of lime, NaOH, KOH, LiOH, $Mg(OH)_2$, NaOR, KOR, $Mg(OR)_2$, $Ca(OR)_2$, LiOR, $Na_2CO_3$, $CaCO_3$, $K_2CO_3$, $Li_2CO_3$ and $MgCO_3$ wherein R is an alkyl.

7. The process of claim 6 in which the base is lime.

8. The process of claim 1 in which the alcohol is a primary alcohol.

9. The process of claim 8 in which the alcohol is methanol.

10. The process of claim 8 in which the alcohol is n-butanol.

11. The process of claim 1 in which the dichloropropene and the alcohol are contacted at a temperature of at most about 250° C.

12. The process of claim 1 in which the dichloropropene and the alcohol are contacted at a temperature within the range of about 60° C. to about 150° C.

13. The process of claim 1 in which the dichloropropene and the alcohol are contacted at a pressure of at most 500 psig.

14. The process of claim 1 in which the dichloropropene and the alcohol are contacted at a pressure within the range of about atmospheric to about 250 psig.

15. The process of claim 1 in which step (d) is carried out at a temperature within the range of about 400° to about 600° C.

16. The process of claim 1 in which step (d) is carried out a temperature within the range of about 450° to about 525° C.

17. A process for upgrading the heavy ends by-products formed during the preparation of allyl chloride comprising the steps of:
   (a) providing a heavy ends by-product stream comprising a dichloropropene and dichloropropane from a chlorination reaction of propylene with a chlorinating agent;
   (b) contacting said dichloropropene and an alcohol in the presence of an effective amount of a base to form an ether intermediate;
   (c) heating said ether intermediate and said dichloropropane at an effective temperature to produce allyl chloride; and
   (d) recovering the allyl chloride.

18. The process of claim 17 in which the base is selected from the group consisting of alkali metal hydroxides, alkaline earth metal hydroxides, alkali metal alkoxides, alkaline earth metal alkoxides, alkali metal carbonates and alkaline earth metal carbonates.

19. The process of claim 18 in which the base is selected from the group consisting of lime, NaOH, KOH, LiOH, $Mg(OH)_2$, NaOR, KOR, $Mg(OR)_2$, $Ca(OR)_2$, LiOR, $Na_2CO_3$, $CaCO_3$, $K_2CO_3$, $Li_2CO_3$ and $MgCO_3$ wherein R is an alkyl.

20. The process of claim 19 in which the base is lime.

21. The process of claim 17 in which the alcohol is a primary alcohol.

22. The process of claim 17 in which the dichloropropene and the alcohol are contacted at a temperature of at most about 250° C.

23. The process of claim 17 in which step (c) is carried out at a temperature within the range of about 400° to about 600° C.

24. The process of claim 17 in which step (c) is carried out at a temperature within the range of about 450° to about 525° C.

25. The process of claim 17 in which the chlorinating agent is chlorine.

* * * * *